(12) United States Patent
Parthasaradhi et al.

(10) Patent No.: US 7,504,516 B2
(45) Date of Patent: Mar. 17, 2009

(54) CRYSTALLINE FORMS OF CANDESARTAN CILEXETIL

(75) Inventors: Reddy Bandi Parthasaradhi, Hyderabad (IN); Reddy Kura Rathnakar, Hyderabad (IN); Reddy Rapolu Raji, Hyderabad (IN); Reddy Dasari Muralidhara, Hyderabad (IN); Reddy Kesireddy Subash Chander, Hyderabad (IN)

(73) Assignee: Hetero Drugs Limited, Hyderabad (IN)

( * ) Notice: Subject to any disclaimer, the term of this patent is extended or adjusted under 35 U.S.C. 154(b) by 324 days.

(21) Appl. No.: 10/509,141

(22) PCT Filed: Mar. 27, 2003

(86) PCT No.: PCT/IN03/00090

§ 371 (c)(1),
(2), (4) Date: Sep. 27, 2004

(87) PCT Pub. No.: WO2004/085426

PCT Pub. Date: Oct. 7, 2004

(65) Prior Publication Data

US 2005/0182114 A1    Aug. 18, 2005

(51) Int. Cl.
*C07D 257/00*    (2006.01)
(52) U.S. Cl. ..................................... 548/253
(58) Field of Classification Search ................ 514/381; 548/253
See application file for complete search history.

(56) References Cited

U.S. PATENT DOCUMENTS

| 4,602,017 | A  | 7/1986 | Sawyer et al. |
| 5,196,444 | A  | 3/1993 | Naka et al. |
| 2004/0102523 | A1 | 5/2004 | Broquaire et al. |

FOREIGN PATENT DOCUMENTS

| EP | 0668272 A2 | 8/1995 |
| EP | 0881212 A1 | 12/1998 |
| WO | WO 02/068398 A1 | 9/2002 |
| WO | WO 2004/083191 A1 | 9/2004 |

OTHER PUBLICATIONS

Brittain, Pharmaceutical Solids, Drugs and the Pharmaceutical Science; 1999, V. 95, pp. 348-361.*
U.S. Department of Health and Human Service, Guidance for Industry, May 15, 2001.*
PCT International Search Report dated Mar. 17, 2003.
Solid-State Characterizaiton of Candesartan Cilexetil (TCV-116): Crystal Structure and Molecular Mobility (Chemical & Pharmaceutical Bulletin (1999), 47(2), 182-186.

* cited by examiner

*Primary Examiner*—Rei-tsang Shiao
(74) *Attorney, Agent, or Firm*—Caesar, Rivise, Bernstein, Cohen & Pokotilow, Ltd.

(57) ABSTRACT

The present invention relates to two novel crystalline forms and a novel 1,4-dioxane solvate of candesartan cilexetil, to processes for their preparation and to pharmaceutical compositions containing them.

9 Claims, 3 Drawing Sheets

CRYSTALLINE FORMS OF CANDESARTAN CILEXETIL

This application is a 371 of PCT/IN03/0090 filed on Mar. 27, 2003.

FIELD OF THE INVENTION

The present invention relates to two novel crystalline forms and a novel 1,4-dioxane solvate of candesartan cilexetil, to processes for their preparation and to pharmaceutical compositions containing them.

BACKGROUND OF THE INVENTION

Candesartan cilexetil of formula (1):

or 2-Ethoxy-1-[[2'-(1H-tetrazol-5-yl)[1,1'-biphenyl]-4-yl] methyl]-1H-benzimidazole-7-carboxylic acid, 1-[[(Cyclohexyloxy)carbonyl]oxy]ethyl ester. Candesartan cilexetil is an antihypertensive agent and its therapeutic uses were disclosed in U.S. Pat. No. 5,196,444. U.S. Pat. No. 5,196,444 also disclosed a crystalline form of candesartan cilexetil (C-type crystalline form). Two crystalline forms of candesartan cilexetil, form I and form II, are described in Chem. Pharm. Bull. 47(2), 182-186 (1999).

We have discovered a novel 1,4-dioxane solvate of candesartan cilexetil and two novel crystalline forms of candesartan cilexetil. The novel forms have been found to be stable and reproducible.

The object of the present invention is to provide a stable novel 1,4-dioxane solvate of candesartan cilexetil and two stable crystalline forms of candesartan cilexetil, processes for preparing these forms and pharmaceutical compositions containing them.

DETAILED DESCRIPTION OF THE INVENTION

One aspect of the present invention is to provide a novel 1,4-dioxane solvate of candesartan cilexetil (hereinafter referred to as candesartan cilexetil dioxane solvate). Typically the content of 1,4-dioxane in the solvate is 8.8 to 13.0% w/w. The candesartan cilexetil dioxane solvate is characterized by an x-ray powder diffraction pattern having peaks expressed as 2θ at about 6.0, 10.7, 16.2, 18.0, 19.7, 20.6, 21.3, 21.7, and 22.3 degrees. FIG. 1 shows typical x-ray powder diffraction pattern of candesartan cilexetil dioxane solvate.

Candesartan cilexetil dioxane solvate is prepared by dissolving crystalline form or amorphous form of candesartan cilexetil in 1,4-dioxane and crystallizing at 5° C. to 15° C., preferably at 5° C. to 10° C.

Another aspect of the present invention is to provide a novel crystalline form of candesartan cilexetil (hereinafter referred to as candesartan cilexetil form III, characterized by an x-ray powder diffraction pattern having peaks at about 6.3, 7.3, 8.1, 8.9, 10.1, 14.6, 15.0, 15.8, and 18.8 degree. FIG. 2 shows typical x-ray powder diffraction pattern of candesartan cilexetil form III.

The candesartan cilexetil form III is prepared by dissolving candesartan cilexetil in toluene by heating, cooling the solution slowly to 0° C. to 5° C., maintaining at 0° C. to 5° C. for about 1 hour and separating the crystals formed by filtration. The solvent may be heated to dissolve candesartan cilexetil. Candesartan cilexetil used in the process may be any of the crystalline forms except form III, amorphous form or candesartan cilexetil dioxane solvate.

Another aspect of the present invention is to provide a novel crystalline form of candesartan cilexetil (hereinafter referred to as candesartan cilexetil form IV). The candesartan cilexetil form IV is characterized by an x-ray powder diffraction pattern having peaks at about 6.1, 7.1, 11.6, 11.9, 17.9, 19.8 and 21.2 degree. FIG. 3 shows typical x-ray powder diffraction pattern of candesartan cilexetil form IV.

The candesartan cilexetil form IV is prepared by mixing candesartan cilexetil, methyl tert-butyl ether and methanol at 50° C. 55° C. and maintaining at 20° C. to 25° C. for about 10 hours. Candesartan cilexetil used in the process may be any of the crystalline forms except form IV, amorphous form or candesartan cilexetil dioxane solvate.

Candesartan cilexetil used in the above processes may be obtained by the known methods.

In accordance with the present invention, there is provided a pharmaceutical composition comprising crystalline form III or form IV of candesartan cilexetil and a pharmaceutically acceptable carrier.

Figure 1:
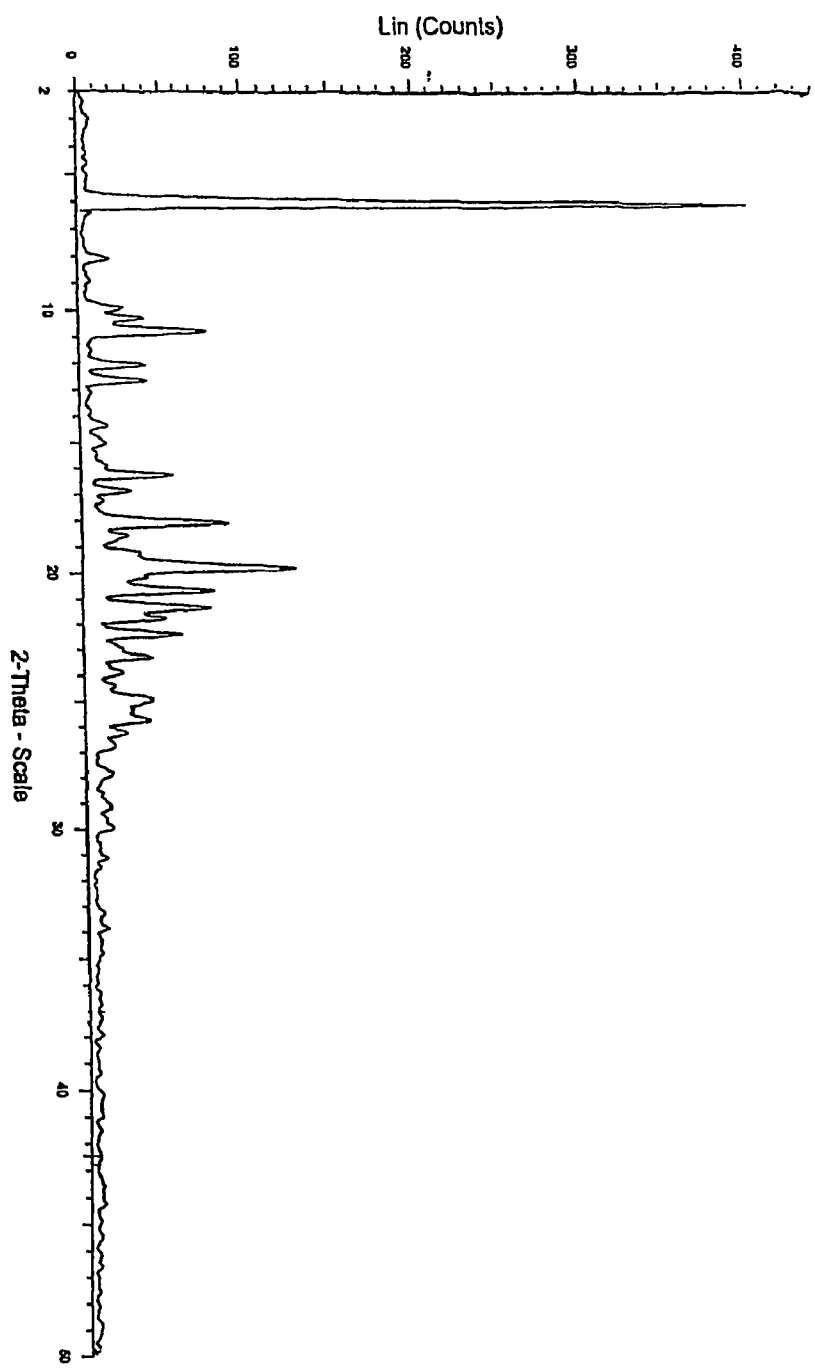
FIG. 1 is a x-ray powder diffraction pattern of candesartan cilexetil dioxane solvate.

x-Ray powder diffraction spectrum was measured on a Siemens D5000 x-ray powder diffractometer having a copper-Kα radiation.

The following examples further illustrate the invention.

EXAMPLE 1

Candesartan cilexetil C-type crystalline form (5 gm, obtained by a process described in U.S. Pat. No. 5,196,444) is dissolved in 1,4-dioxane (50 ml) at 25° C. The solution is cooled to 5° C. and maintained for 4 hours at about 5° C. The separated solid is filtered to yield 3 gm candesartan cilexetil dioxane solvate.

EXAMPLE 2

Candesartan cilexetil C-type crystalline form (5 gm) is added to toluene (25 ml) and heated to reflux. The contents are maintained under reflux for 15 minutes and then cooled slowly to 0° C. in 1 hour and maintained at 0° C. to 5° C. for 1 hour. The separated crystals are collected by filtration to give 3.5 gm candesartan cilexetil form III.

EXAMPLE 3

Example 1 is repeated using candesartan cilexetil form III instead of candesartan cilexetil C-type crystalline form to give Candesartan cilexetil dioxane solvate.

EXAMPLE 4

The mixture of candesartan cilexetil C-type crystalline form (5 gm), methyl tert-butyl ether (50 ml) is heated to 55° C., methanol (17 ml) is added to the mixture at 55° C. and maintained at about this temperature for 1 hour. The contents are cooled to 25° C. and maintained at about 25° C. for 13 hours. The separated solid is collected by filtration to give 3 gm candesartan cilexetil form IV.

EXAMPLE 5

Example 2 is repeated using-candesartan cilexetil form IV instead of candesartan cilexetil C-type crystalline form to give Candesartan cilexetil form III.

EXAMPLE 6

Example 4 is repeated using candesartan cilexetil dioxane solvate instead of candesartan cilexetil C-type crystalline form to give Candesartan cilexetil form IV.

We claim:

1. A candesartan cilexetil 1,4-dioxane solvate, characterized by an x-ray powder diffraction pattern having peaks expressed as 2θ at about 6.0, 10.7, 16.2, 18.0, 19.7, 20.6, 21.3, 21.7, and 22.3 degrees.

2. The candesartan cilexetil 1,4-dioxane solvate of claim 1, wherein the content of 1,4-dioxane is 8.8 to 13.0% w/w.

3. Candesartan cilexetil 1,4-dioxane solvate of claim 1, further characterized by an x-ray powder diffraction pattern as in FIG. 1.

4. The process for the preparation of candesartan cilexetil 1,4-dioxane solvate of claim 1, which comprises:
    a) dissolving candesartan cilexetil in 1,4-dioxane; and
    b) crystallizing candesartan cilexetil as 1,4-dioxane solvate from the solution at 50° C. to 15° C.

5. The process according to claim 4, wherein candesartan cilexetil used is a crystalline form of candesartan cilexetil.

6. The process according to claim 5, wherein the crystalline form of candesartan cilexetil is candesartan cilexetil form III.

7. A crystalline candesartan cilexetil form III, characterized by an x-ray powder diffraction pattern having peaks expressed as 2θ at about 6.3, 7.3, 8.1, 8.9, 10.1, 14.6, 15.0, 15.8, and 18.8 degrees.

Figure 2:
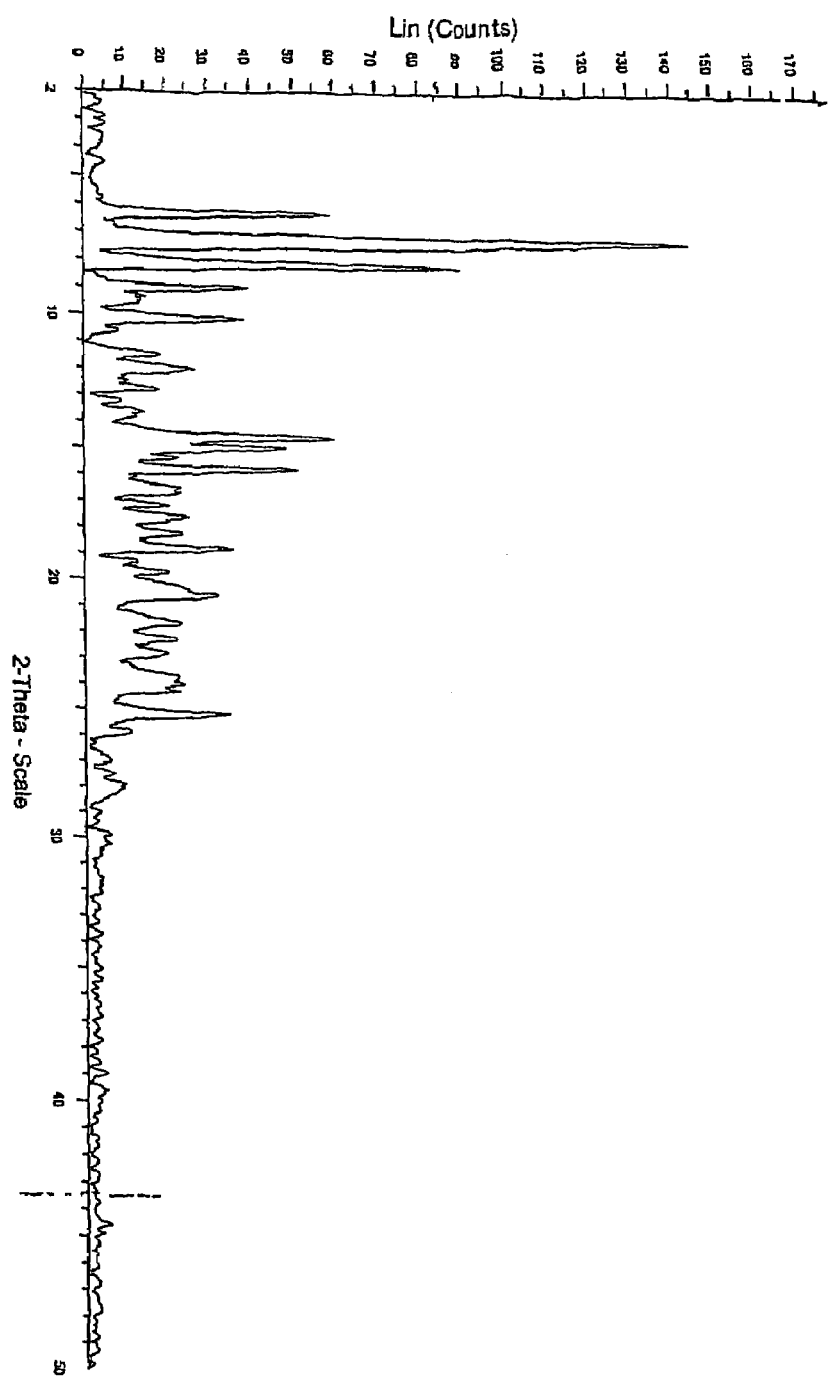
FIG. 2 is a x-ray powder diffraction pattern of candesartan cilexetil form III.
Figure 3:
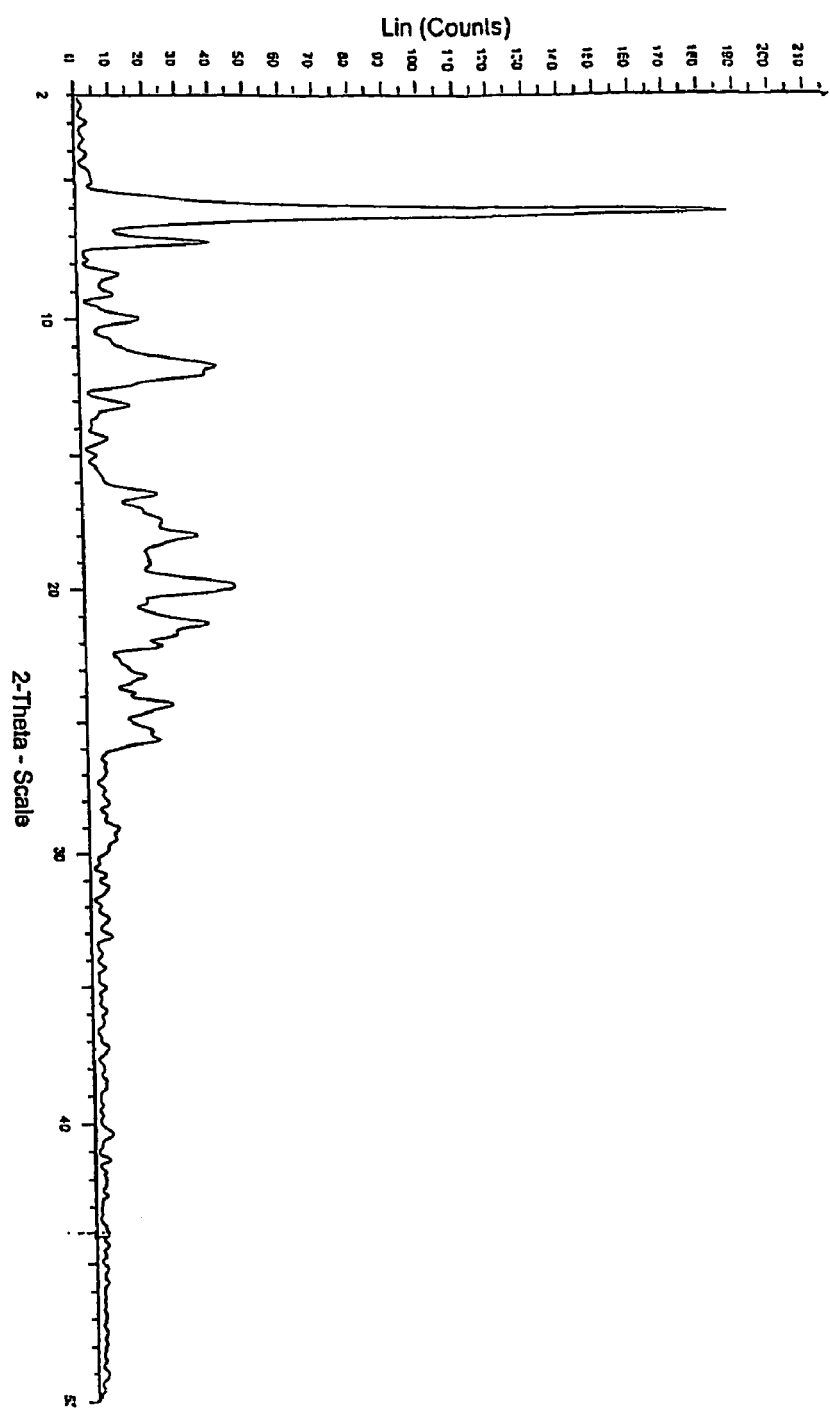
FIG. 3 is a x-ray powder diffraction pattern of candesartan cilexetil form IV.

8. Candesartan cilexetil form III of claim 7, further characterized by an x-ray powder diffraction pattern as in FIG. 2.

9. The process for the preparation of candesartan cilexetil form III of claim 7, which comprises:
    a) mixing candesartan cilexetil 1,4-dioxane solvate of claim 1 with toluene;
    b) heating to obtain clear solution;
    c) cooling slowly to 0° C. to 5° C. in about 1 hour;
    d) maintaining at 0° C. to 5° C. for about 1 hour; and
    e) filtering the separated solid.

* * * * *